United States Patent [19]

Craig et al.

[11] Patent Number: 4,810,630

[45] Date of Patent: Mar. 7, 1989

[54] USE OF POLYOXYETHYLENE ETHERS TO IMPROVE THE PERFORMANCE OF IMMUNOASSAYS EMPLOYING PEROXIDASE CONJUGATES

[75] Inventors: Alan R. Craig, Wilmington; Thomas P. Hartz, Jr., Newark, both of Del.

[73] Assignee: E. I. Du Pont de Nemours and Company, Wilmington, Del.

[21] Appl. No.: 31,932

[22] Filed: Mar. 30, 1987

[51] Int. Cl.$^4$ .................... G01N 33/571; G01N 1/00; C12Q 1/28; C12N 9/96

[52] U.S. Cl. .......................... 435/7; 435/28; 435/188; 436/511; 436/825; 436/175

[58] Field of Search .................. 435/4, 7, 28, 188; 436/511, 537, 818, 826, 825, 175

[56] References Cited

U.S. PATENT DOCUMENTS 4,454,232  6/1984  Breglio et al. ............... 436/504
4,525,452  6/1985  Jones et al. ................. 435/7

OTHER PUBLICATIONS

Hautanen, A., and E. Linder, "C3c-Binding ELISA for the Detection of Immunoconglutinins and Immunoglobulin Aggregates". In Methods in Enzymology. vol. 74, Part C. (Langone, ed) 1981, pp. 600–601.

Qualitiere et al., *J. Immunology,* vol. 119 (5), pp. 1645–1651 (1977).

Porstmann et al., *Clinica Chimica Acta,* vol. 109, pp. 175–181 (1981).

*Primary Examiner*—Robert J. Warden
*Assistant Examiner*—Toni R. Scheiner

[57] ABSTRACT

Signal to noise ratio of enzyme immunoassays employing peroxidase conjugates can be improved by including polyoxyethylene ether detergent in the assay buffer. Such detergents reduce interference due to blood and also improve sensitivity of assays of blood-free samples.

5 Claims, No Drawings

USE OF POLYOXYETHYLENE ETHERS TO IMPROVE THE PERFORMANCE OF IMMUNOASSAYS EMPLOYING PEROXIDASE CONJUGATES

BACKGROUND OF THE INVENTION

1. Technical Field

This invention relates to enzyme immunoassays using peroxidase conjugates and, in particular, to improvements in the sensitivity and specificity of such immunoassays provided by polyoxyethylene ether detergents, especially Triton ® X-100.

2. Background Art

The use of antibodies labeled with horseradish peroxidase in immunochemical techniques was first described in 1966 [PK Nakane et al., J. Histochem Cytochem., Volume 14(12), pp. 929–31 (1966)]. The enzyme-linked immunosorbent assay [ELISA] technique was described in 1971 [E. Engvall et al., Immunochemistry, Volume 8(9), pp. 871–4 (1971)]. Horseradish peroxidase remains an important enzyme for labeling antibodies and antigens in a variety of immunochemical techniques because of its ability to rapidly react with substrates which generate easily detectable materials and the relative ease with which the enzyme can be coupled to immunochemicals with the retention of its enzymatic activity. Improvements in enzyme immunoassay technology have concentrated on the development of more specific antibodies with higher binding affinities for their antigens, enzymes demonstrating a faster turnover rate of their substrates, and better means to link antibodies and enzymes with the retention of the activities of both partners.

The sensitivity of an immunoassay can be defined by the ratio of the specific signal generated to the background noise of the system. Factors increasing assay noise include non-specific binding of labeled antibody to various components of the assay and the activity of some endogenous component of the assay matrix which reacts with the enzyme substrate to yield a reaction product interfering with the accurate detection of product formed by the labeled antibody-antigen complex. Typically, additives such as detergents, non-reactive proteins, or salts are added to the assay matrix to lower assay noise by reducing non-specific binding of the enzyme-antibody conjugate or other potentially interfering component to the assay matrix.

Non-ionic detergents are most frequently included in buffer matrices of enzyme immunoassays to reduce noise. Qualtiere et al. [J. Immunology, Volume 119(5), pp. 1645–51 (1977)] suggested that, as a class, non-ionic detergents bind water-soluble proteins at only a few high-affinity sites and that this binding does not generally result in a denaturing effect. These investigators observed that, whereas deoxycholate and dodecylsulfate, ionic detergents, interfered with antigen-antibody reactions, Triton ® X-100 (Rohm & Haas Co., Philadelphia, PA), Nonidet ® P-40 (Shell Co., Houston, TX), Tween ® 20 (Atlas Chemical Industries, Inc., Wilmington, DE), Sterox ® SL (Monsanto Co., St. Louis, MO), and Brij ®-35 (Atlas Chemical Industries, Inc., Wilmington, DE), all non-ionic detergents, did not. U.S. Pat. No. 4,454,232 issued to Breglio et al. on June 7, 1982, claims the use of a non-ionic detergent and a surface active agent to reduce the effects of variable serum protein content of samples which leads to inaccurate estriol immunoassay determinations.

Non-ionic detergents have been shown in several reports to increase the activity of horseradish peroxidase. Porstmann et al. [Clin. Chem. Acta., Volume 109, pp. 175–81 (1981); J. Clin. Chem. Clin. Biochem., Volume 19. pp. 435–39 (1981); Z Med. Laboratoriumsdiagn. Volume 21(3), pp. 180–181 (1980)] found that the inclusion of non-ionic detergents such as polyoxyethylene-octylphenol (Triton ® X-100) or -sorbitol ester (Tween ® 20) in the substrate solution increased the activity of horseradish peroxidase.

Various components of whole blood are known to exhibit peroxidase-like activity which can manifest itself in an enzyme immunoassay using a peroxidase labeled immunoreagent as an increased level of background activity. The amount of these components can vary widely between patient samples. For example, the amount of blood collected on a urogenital swab for the detection of *Neisseria gonorrhea* antigen can vary depending on the menstrual cycle of the female patient, the degree of infection, or the extent of irritation generated during the taking of the sample. For immunoassays using a visual color change of a peroxidase reactive substrate/chromogen system as a marker of infection, a false positive result may be reported due to the presence of blood. With instrumentally evaluated systems, blood may result in a signal exceeding the threshold level of reactivity and again yield a false positive result. Conversely, eliminating the noise due to blood interference in an immunoassay should increase assay sensitivity by increasing the signal to noise ratio.

SUMMARY OF THE INVENTION

It is the purpose of this invention to provide improved performance of enzyme-linked immunosorbent assays for antigens, haptens or antibodies in patient samples using peroxidase labeled immunoreagents. It has been found that the signal to noise ratio of such assays can be increased through the use of polyoxyethylene ether non-ionic detergents in the assay buffers. Such detergents significantly reduce the interference due to blood and also, surprisingly, improve the sensitivity of the assays both in samples containing blood and in blood-free samples.

DESCRIPTION OF INVENTION

Immunoassays for the detection and/or quantitation of antigenic markers contained in clinical samples are used widely in diagnostic medicine. Antibodies labeled with peroxidase, especially horseradish peroxidase, are frequently employed to indicate the presence of the markers in the sample by the action of the enzyme on peroxidase-specific substrates. There are constituents of whole blood, however, which exhibit peroxidase-like activity and can also act upon the substrate, yielding inaccurate results. In qualitative assays designed to detect the presence of an antigen, such as an immunoassay for an infectious disease, these non-specific reactions can lead to severe consequences, such as the false conclusion that the patient is infected with a pathogen. In quantitative assays designed to estimate the concentration of a particular analyte, such as the concentration of human chorionic gonadotropin (HCG), this non-specific reactivity may lead to the inaccurate diagnosis that the patient is pregnant. Thus it is most important that immunoassays be optimized to reduce or eliminate the contribution of non-specific reactions as well as provide the appropriate response for specific reactions.

It is highly desirable that components of whole blood do not interfere with immunoassays as this may lead to serious misdiagnosis and mistreatment. It is also common that some components of whole blood are contaminants in the samples routinely used for immunoassay. This may result for instance from the use of hemolysed serum or swabs which have been contaminated with small amounts of blood. Surprisingly, we found that polyoxyethylene ether detergents, especially Triton ®  X-100, are superior reagents for reducing or eliminating, this interference. Triton ®-100 is a polyoxyethylene octylphenyl ether. Other polyoxyethylene ethers with a variety of hydrocarbon chain lengths, including lauryl, cetyl, oleyl, stearyl and tridecyl ethers, can be used to improve performance. Assay conditions, reagents and configurations can be optimized for a particular polyoxyethylene ether. The reason for the superior performance of these detergents is not known, but may be due to a superior ability to solubilize the specific components of whole blood which cause the interference. The interference itself appears to be due to peroxidase like activity which is present in whole blood. As little as 4 volume percent blood in a patient sample can cause a false positive result.

The immunoassays of this invention use an effective level of a polyoxyethylene ether detergent in the assay buffer and reagent buffers to reduce or eliminate this interference. Effective concentrations are generally between 0.03 and 3.0% by weight, but concentrations as low as 0.02% have been found effective in some circumstances. Selection of the optimum or preferred concentrations may be done in many ways. These ways will be obvious to one skilled in the art of developing immunoassays as they are the same techniques and procedures used to optimize other components of the immunoassay. These may be simple linear optimization experiments or complex multivariable optimizations such as those described by Box et al. [J. Royal Statistical Society, Series B, 1–45 (1951)]. Typically, a broad optimum is observed, such as 0.05–1.5%. A representative procedure is described below.

An assay buffer is prepared which contains the appropriate concentration of buffers and salts, such as a phosphate buffered saline solution, a quantity of a non-specific protein, such as serum albumin, and a polyoxyethylene ether detergent. The concentrations of buffer, salt, and non-specific protein are optimized to yield maximal signal and minimal background response in the enzyme immunoassay in which the assay buffer will be applied. A quantity of polyoxyethylene ether detergent is added at a concentration determined in a similar optimization experiment. The resulting optimized assay buffer is used as a reagent buffer during the incubation steps of the immunoassay, such as during the step in which the patient sample solution is incubated with a surface coated with antibody specific for the antigen being detected and during the step in which the peroxidase labeled antibody is permitted to bind to the captured antigen. A further advantage may be realized by including a polyoxyethylene ether detergent in any wash solutions used to remove nonspecifically bound materials and during the incubation with the enzyme substrate/chromogen solution.

Another unexpected advantage of this invention is that in addition to reduction or elimination of this interference, the inclusion of polyoxyethylene ether detergents as described above leads to an enhancement of the specific assay response. That is, for a given level of analyte and immunoreagents, a larger signal is obtained in the presence of said detergents than in the absence. Again, these polyoxyethylene ether detergents, especially Triton ® X-100, are unexpectedly superior in this respect. This enhancement effect is obtained even if the detergents are not included in the assay buffer while the substrate/chromogen is exposed to the peroxidase enzyme. The reason for the superior performance is not known. but may be related to some specific binding of the detergent to the peroxidase enzyme.

A still further advantage of this invention is that for immunoassays in which an insoluble support is coated with a specific antibody and the coated support is used to capture an analyte from a sample, a reduction in the quantity of antibody required to achieve the maximum signal has been found. As demonstrated below the maximum assay signal to noise ratio is achieved when polyoxyethylene ether detergents are used in the assay and reagent buffer solutions.

EXAMPLE 1

(a) Description of assay:

Samples containing *Neisseria gonorrhea* were treated for two (2) minutes with one part 1.0N NaOH to expose the antigen recognized by the anti-*N. gonorrhea* antibody in an immunoassay for the detection of gonorrheal infection. Four parts of 0.5M phosphate buffer, pH 6.0, containing 0.06M NaCl, 0.5% bovine serum albumin and detergent were added. Aliquots, 0.500 mL, of the neutralized, treated samples were placed in 12×75 mm test tubes and 50 μL of horseradish peroxidase conjugated antibody, specific for *N. gonorrhea*, was added. A multifinned plastic dipstick (U.S. Pat. No. 4,135,884 issued June 23, 1979 to Shen) was coated with anti-*N. gonorrhea*, by incubating the dipstick in an antibody solution, 2–5 μg/mL in phosphate buffered saline, for two hours at room temperature then blocked by incubation with a solution containing 0.5% bovine serum albumin and 20% sucrose for two hours at room temperature and dried. One dipstick was added to each tube. The tubes were incubated at room temperature for 30 minutes. After the incubation, the dipsticks were removed and washed thoroughly with cold running tapwater and transferred to another test tube containing 500 μL of a citrate/phosphate buffer solution containing 1.56 mM 3,3′,5,5′-tetramethylbenzidine, 0.02% $H_2O_2$, and 30% methyl alcohol, pH 5.0. The dipsticks were incubated in the substrate/chromogen solution for ten (10) minutes, then discarded. The assay was reported to be positive if any visible blue color was observed in the substrate/chromogen solution in comparison to a control for which a sample containing no *N. gonorrhea* was processed as described. Alternatively, a 200 μL portion of the incubated substrate/chromogen solution was transferred to a microtiter plate and the optical density of the solution measured at 630 nm, and corrected for the optical density at 490 nm.

(b) Detergent studies:

The non-ionic detergents polyoxyethylene-octylphenoxy (Triton ® X-100), polyoxyethylene-sorbitan monolaurate (Tween ® 20), and the anionic detergent N-lauroylsarcosine (Sarkosyl ®) were compared for their effect on the signal to noise ratio in the assay described above over a range of detergent concentrations. Neutralized, treated samples containing $4\times10E5$ and $4\times10E6$ organisms/mL *N. gonorrhea* and *Bramhamella* catarrhalis, respectively, were run as positive (signal) and negative (noise) specimens. The assay was run in both the absence of blood and in the presence of 50 μL/mL whole blood. Table 1 lists the signal to noise ratios for these specimens at varying detergent concentrations in the absence and presence of blood. Sarkosyl ® decreased the response for negative samples in the presence of blood but also reduced the specific signal to gonorrhea in both the presence and absence of blood. Tween ® 20 increased the specific response to gonorrhea both in the presence and absence of blood but was ineffective in reducing the interference due to blood. Triton ® X-100 both decreased the interference due to blood and increased the specific response both in the presence and absence of blood. For samples containing blood, signal to noise ratios were an order of magnitude greater with 0.3% Triton ® X-100 than Tween ® 20. The absorbances are reported in Table 2.

TABLE 1

Elimination of Interference due to Blood

| Detergent | Conc. | Signal/Noise Without Blood | With 50 μL Blood |
|---|---|---|---|
| Triton ® X-100 | 0.05% | 41.8 | 1.08 |
|  | 0.10% | 77.5 | 4.11 |
|  | 0.20% | 78.7 | 3.51 |
|  | 0.25% | >71 | 18.5 |
|  | 0.30% | >108 | 24.1 |
| Tween ® 20 | 0.075% | 9.48 | 0.94 |
|  | 0.125% | 21.7 | 1.02 |
|  | 0.200% | 24.8 | 2.42 |
| Sarkosyl ® | 0.20% | 25.2 | 2.56 |
|  | 0.30% | 22.9 | 6.00 |
|  | 0.40% | 34.6 | 6.53 |

TABLE 2

Effect of Detergents on Specific Signal and Noise

| | Sample Absorbance (Mean of Triplicate Determinations) | | | |
|---|---|---|---|---|
| Detergent % Conc. | Negative (Noise) | | Positive (Signal) | |
|  | B. cat. + 0 μL blood | B. cat. + 50 μL blood | N. gon. + 0 μL blood | N. gon. + 50 μL blood |
| Triton ® X-100 | | | | |
| 0.100% | 0.020 | 0.095 | 1.550 | 0.390 |
| 0.200% | 0.021 | 0.142 | 1.653 | 0.498 |
| 0.300% | 0.017 | 0.112 | >1.836 | 1.083 |
| Tween ® 20 | | | | |
| 0.075% | 0.029 | 0.502 | 0.275 | 0.473 |
| 0.125% | 0.020 | 0.508 | 0.434 | 0.520 |
| 0.200% | 0.032 | 0.251 | 0.794 | 0.607 |
| Sarkosyl ® | | | | |
| 0.200% | 0.036 | 0.480 | 0.907 | 1.227 |
| 0.300% | 0.021 | 0.114 | 0.480 | 0.684 |
| 0.400% | 0.010 | 0.086 | 0.346 | 0.562 |

Optimal concentrations of Tween ® 20 (0.1%) and Triton ® X-100 (0.3%) were compared for their ability to reduce the non-specific signal due to varying quantities of blood. Table 3 presents the results of the assay using a 4×10E6 sample of B. catarrhalis in the presence of increasing quantities of whole blood. Visible blue color is reported by most laboratorians at optical densities above the threshold range of 0.025 to 0.035. As shown in Table 3, that level is exceeded when Tween ® 20 buffer is used with 5 μL of blood. As little as 4 volume percent of blood in a patient sample will yield a positive result from some laboratorians. Assay buffer containing Triton ® X-100 can accommodate as much as 20 μL of blood without yielding a false positive result in a visually read test.

TABLE 3

Effect of Blood on Assay Response to Negative Samples

| Volume of Blood Added (μL) | Absorbance | |
|---|---|---|
|  | Triton ® X-100 | Tween ® 20 |
| 0 | 0.000 | 0.020 |
| 1 | ND | 0.028 |
| 2 | ND | 0.035 |
| 4 | ND | 0.036 |
| 5 | 0.000 | ND |
| 8 | ND | 0.056 |
| 10 | 0.005 | ND |
| 16 | ND | 0.124 |
| 20 | 0.015 | ND |
| 40 | 0.039 | ND |
| 80 | 0.037 | ND |

(ND = NOT DONE)

EXAMPLE 2

(a) Description of Assay

Samples were treated 1.0N NaOH and neutralized with assay buffer as described in Example 1, above. For this assay, 0.100 mL aliquots of the treated, neutralized sample were transferred to the wells of a 96-well microtiter plate which had been previously incubated with an optimized concentration of anti-N. gonorrhea antibody diluted in phosphate buffered saline for 90–120 minutes, drained, then blocked with a solution containing 1.0% bovine serum albumin and 20% sucrose in phosphate buffered saline for 2 hours and dried in vacuo. The aliquots were permitted to incubate in the microtiter plate wells for 90 minutes at room temperature, then drained and washed with phosphate buffered saline containing 0.05% Tween ® 20. Horseradish peroxidase conjugated anti-N. gonorrhea, 100 μL of an optimized concentration, was then added to each well and the plate again incubated for 1 hour at room temperature. The plate was then drained and washed as above. A 100 μL portion of the substrate/chromogen solution described in Example 1, above, was then added to each well and incubated for 10 minutes at room temperature. The absorbance of each well was then determined at 630 nm, and corrected for the absorbance at 490 nm.

(b) Optimization of coating antibody concentration:

Antibody specific for Neisseria gonorrhea was used to coat the wells of microtiter plates at varying concentrations in phosphate buffered saline, as described above. A comparison of the optimal antibody concentration in assays using Tween ® 20 or Triton ® X-100 was made by testing a single concentration of N. gonorrhea in wells previously coated, blocked, and dried as described above. The optimum concentration of antibody is identified as that which yields the maximum signal in the assay with a minimal background response. Table 4 lists the results of such experiments using Tween ® 20 and Triton ® X-100 as detergents in the assay buffer. The maximum response is achieved at much lower antibody coatings in the presence of Triton ® X-100 than in the presence of Tween ® 20.

TABLE 4

Optimization of Coating Antibody Concentration

| Detergent | Antibody Concentration (μg/well) | % Maximum Signal | Absorbance Background |
|---|---|---|---|
| Tween ® 20 | 2.0 | 66 | 0.034 |
| | 1.5 | 77 | 0.022 |
| | 1.0 | 90 | 0.050 |
| | 0.8 | 98 | 0.018 |
| | 0.5 | 100 | 0.013 |
| | 0.1 | 35 | 0.005 |
| | 0.05 | 16 | 0.001 |
| Triton ® X-100 | 0.60 | 57 | 0.019 |
| | 0.50 | 58 | 0.020 |
| | 0.45 | 66 | 0.021 |
| | 0.40 | 69 | 0.022 |
| | 0.35 | 70 | 0.019 |
| | 0.30 | 98 | 0.016 |
| | 0.20 | 100 | 0.016 |

We claim:

1. In an enzyme-linked immunosorbent assay for an analyte in a patient sample comprising
    (a) incubating the sample in an aqueous assay buffer with an analyte-specific immunoreagent bound to a support, to capture the analyte on the support, and simultaneously or subsequently,
    (b) incubating the captured analyte with peroxidase-labeled analyte-specific immunoreagent to bind labeled immunoreagent to the support,
    (c) separating bound and unbound labeled immunoreagent,
    (d) adding peroxidase substrate solution to the bound, labeled immunoreagent and measuring the resulting enzymatic reaction, wherein the patient sample contains blood in sufficient quantity to interfere with immunoassay results, the improvement comprising including in the assay buffer a polyoxyethylene ether detergent in an amount sufficient to improve the signal to noise ratio of the assay.

2. Improved assay of claim 1 wherein the sample is contaminated with greater than 4 volume percent blood, the detergent is polyoxyethyleneoctylphenol and the amount of detergent is between about 0.03 and 3% by weight of the buffer solution.

3. Improved assay of claim 2 wherein the immunoreagent is an antibody to the analyte.

4. Improved assay of claim 3 wherein the analyte is an infectious microorganism.

5. Improved assay of claim 4 wherein the microorganism is *N. gonorrhea*.

* * * * *